United States Patent
Saito et al.

(10) Patent No.: US 9,376,384 B2
(45) Date of Patent: Jun. 28, 2016

(54) DIARYLIODONIUM SALT

(71) Applicant: UBE INDUSTRIES, LTD., Yamaguchi (JP)

(72) Inventors: Norimichi Saito, Yamaguchi (JP); Norio Shibata, Aichi (JP); Kohei Matsuzaki, Aichi (JP); Kenta Okuyama, Aichi (JP)

(73) Assignee: UBE INDUSTRIES, LTD. (JP)

( * ) Notice: Subject to any disclaimer, the term of this patent is extended or adjusted under 35 U.S.C. 154(b) by 0 days.

(21) Appl. No.: 14/825,169

(22) Filed: Aug. 13, 2015

(65) Prior Publication Data

US 2016/0046566 A1    Feb. 18, 2016

(30) Foreign Application Priority Data

Aug. 13, 2014 (JP) ................. 164814/2014

(51) Int. Cl.
| | |
|---|---|
| *C07C 323/09* | (2006.01) |
| *C07D 209/10* | (2006.01) |
| *C07D 333/18* | (2006.01) |
| *C07D 209/48* | (2006.01) |
| *C07C 309/06* | (2006.01) |
| *C07C 309/30* | (2006.01) |
| *C07C 381/00* | (2006.01) |

(52) U.S. Cl.
CPC .............. *C07C 323/09* (2013.01); *C07C 309/06* (2013.01); *C07C 309/30* (2013.01); *C07C 381/00* (2013.01); *C07D 209/10* (2013.01); *C07D 209/48* (2013.01); *C07D 333/18* (2013.01); *C07C 2102/08* (2013.01)

(58) Field of Classification Search
CPC .................................................. C07C 323/09
See application file for complete search history.

(56) References Cited

PUBLICATIONS

Matsuzaki et al. Org. Lett. 2015, 17, 3038-3041.*
Allen, Anna E. et al. (2011) "Enantioselective α-Arylation of Aldehydes via the Productive Merger of Iodonium Salts and Organocatalysis" J. Amer. Chem. Society, vol. 133, pp. 4260-4263.
Bigot, Aurelien et al. (2011) Enantioselective α-Arylation of N-Acyloxazolidinones with Copper (II)-bisoxazoline Catalysts and Diaryliodonium Salts, J. Amer. Chem Society, vol. 133, pp. 13778-13781.

* cited by examiner

*Primary Examiner* — Matthew Coughlin
(74) *Attorney, Agent, or Firm* — Swanson & Bratschun, L.L.C.

(57) ABSTRACT

Provided is a compound that allows easy introduction of a pentafluorosulfanylaryl group into a compound of interest. A diaryliodonium salt is represented by the general formula (d) shown below:

[Formula]

$$(R^1)_m \underset{(F_5S)_k}{\overset{}{\text{Ar}}} - \overset{\oplus}{\underset{}{I}} - \text{Ar}(R^2)_n \quad A^{\ominus} \quad (d)$$

In this formula, k is 1 or 2, $R^1$ is an alkyl group having 1 or 2 carbon atoms, m is an integer of 0 to 4, $R^2$ is a straight or branched alkyl group having 1 to 4 carbon atoms, n is an integer of 0 to 5, and $A^-$ is a counter anion.

7 Claims, No Drawings

DIARYLIODONIUM SALT

TECHNICAL FIELD

The present invention relates to a diaryliodonium salt. More particularly, this invention relates to a diaryliodonium salt and a process for introducing an aryl group containing a pentafluorosulfanyl group into a compound through the use of said diaryliodonium salt.

BACKGROUND ART

The pentafluorosulfanyl ($SF_5$) group is known to exhibit a strong electron-withdrawing property due to the presence of fluorine atoms, and also to have high lipophilicity. Thus, compounds containing a $SF_5$ group are expected to be applied to physiologically active substances such as liquid crystal materials and pharmaceutical and agricultural chemicals. However, a process for introducing a $SF_5$ group into a compound of interest is not easy to carry out since this process uses chlorine gas or the like and so requires sophisticated equipment and skilled techniques. Thus, there has hitherto been reported a process for synthesizing a biaryl compound containing a $SF_5$ group by subjecting an aromatic compound containing a $SF_5$ group to coupling reaction in the presence of a transition metal catalyst (Non-patent Literature 1).

CITATION LIST

Non-Patent Literature

Non-patent Literature 1: *Eur. J. Org. Chem.*, 2012, 1504.

SUMMARY OF INVENTION

Technical Problem

However, there has been a need for a simpler process for introducing a $SF_5$ group into a compound of interest. In particular, introducing a pentafluorosulfanyl-containing aryl (hereinafter also called "$ArSF_5$") group, in which a $SF_5$ group is bonded to an aromatic ring, into a compound of interest, if possible, will be of great advantage in pharmaceutical and other fields. In view of these circumstances, the present invention has as its object to provide a compound that allows easy introduction of an $ArSF_5$ group into a compound of interest.

Solution to Problem

The present inventors found that particular diaryliodonium salts can achieve the above-mentioned object, and thus completed the present invention. More specifically, the above-mentioned object is achieved by the present invention as described below.

(1) A diaryliodonium salt of the general formula (d) shown below.
(2) The diaryliodonium salt as set forth in (1), wherein m is 0 and n is 3.
(3) The diaryliodonium salt as set forth in (2), wherein $R^2$ is a methyl group, an ethyl group, a n-propyl group, or an i-propyl group.
(4) The diaryliodonium salt as set forth in (1), wherein m is 0 and n is 0.
(5) A process for preparing the diaryliodonium salt as set forth in any one of (1) to (4), the process comprising:
providing a compound of the general formula (b) shown below; and
subjecting said compound to an oxidation reaction and a Friedel-Crafts reaction with a compound of the general formula (c) shown below at the same time to produce the diaryliodonium salt of the general formula (d).
(6) A process for preparing a compound of the general formula (f) shown below, the process comprising reacting a compound of the general formula (d) shown below with a nucleophilic compound Z to introduce an aryl group containing a pentafluorosulfanyl group into the nucleophilic compound.
(7) The process as set forth in (6), wherein the nucleophilic compound Z is selected from the group consisting of a 1,3-dicarbonyl compound, a phenol compound, an aniline compound, a heterocyclic compound, an alcohol compound, an oxyimide compound, an aromatic sulfur compound, and an aromatic cyanogen compound.

Advantageous Effects of Invention

The present invention can provide a diaryliodonium salt which allows easy introduction of an $ArSF_5$ group into a compound of interest.

DESCRIPTION OF EMBODIMENTS

Hereunder, the present invention will be described in detail. As used in this invention, a numerical range expressed as "X to Y" includes the values at both ends, i.e., X and Y.

1. Diaryliodonium Salt

The diaryliodonium salt of the present invention is represented by the general formula (d) shown below.

[Formula 1]

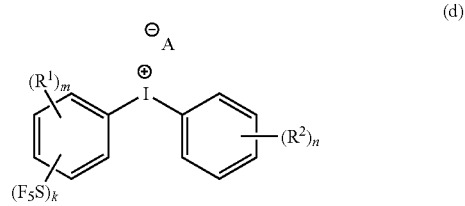

(d)

In this formula, k represents the number of $SF_5$ groups, and is 1 or 2. A $SF_5$ group is preferably bonded to the meta- or para-position of a benzene ring. If k is 2, two $SF_5$ group are preferably bonded to the meta-position of one benzene ring.

$R^1$ is a substituent on one benzene ring and is an alkyl group having 1 or 2 carbon atoms. The symbol m represents the number of $R^1$ substituents and is an integer of 0 to 4. From the viewpoint of reducing steric hindrance, it is preferred that $R^1$ be not present, or in other words, m be 0. However, if $R^1$ is present, it is preferred that $R^1$ be a methyl group and m be 1 or 2.

$R^2$ is a substituent on the other benzene ring and is a straight or branched alkyl group having 1 to 4 carbon atoms. For reasons including ease of synthesis, it is preferred that $R^2$ be a methyl group, an ethyl group, a n-propyl group, or an i-propyl group. The symbol n represents the number of $R^2$ substituents and is an integer of 0 to 5. For the same reasons, it is preferred that n be 3. In this case, $R^2$ substituents are preferably bonded to the ortho- and para-positions. From the viewpoint of availability of source materials, it is preferred that n be 0.

A⁻ is a counter anion. A⁻ influences the solubility of the diaryliodonium salt in a solvent. From this viewpoint, it is preferred that A⁻ be a trifluoromethanesulfonate anion (hereinafter also called "OTf").

2. Process for Preparing a Diaryliodonium Salt

The diaryliodonium salt is preferably prepared according to the scheme shown below.

[Formula 2]

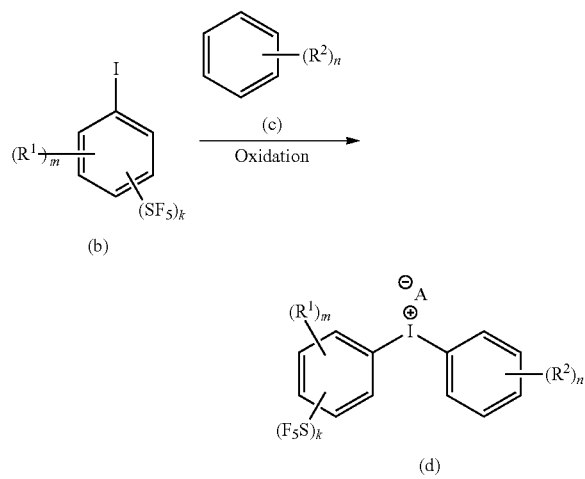

(1) Provision of a Compound (b)

There is first provided a compound (b). In the compound (b), $R^1$, m and k are as defined above. The compound (b) can be prepared by any appropriate procedure, or in other words can be prepared by subjecting a corresponding bromide to an aromatic Finkelstein reaction (*J. Am. Chem. Soc.*, 2002, 124, 14844; and *Chem. Commun.*, 2012, 48, 3993) in the presence of a metal catalyst. To be specific, a bromide (compound (a)) is reacted with NaI in the presence of CuI to produce an iodide. The amount of CuI to be used is in the range of 5 to 20 mol % relative to the bromide, and the amount of NaI to be used can be excessive relative to the bromide, and is preferably in the range of 1.5 to 3 equivalent. In this process, it is preferred to use an amine such as trans-N,N'-dimethyl-1,2-cyclohexane diamine and N,N'-dimethylethylene diamine in an amount of 5 to 20 mol % relative to the bromide. The type of a solvent is not limited, but an ethereal solvent such as dioxane is preferred. The reaction temperature can be adjusted as appropriate but is preferably in the range of 80 to 150° C. Examples of this reaction are shown below.

[Formula 3]

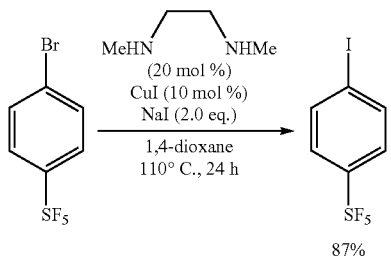

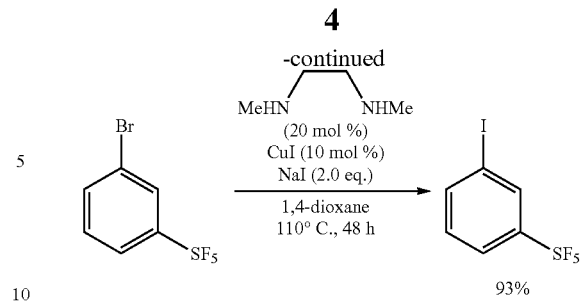

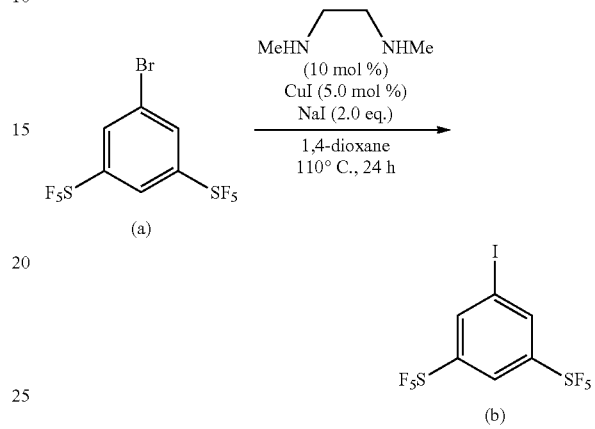

If a $SF_5$ group is bonded to a meta-position in the compound (b), this compound can be synthesized from an aromatic amine. To be specific, this compound can be prepared by a Sandmeyer reaction (Douglas Philp, et al., *Tetrahedron*, 2000, 56, 3399) and a halogen exchange reaction as shown below. An example of these reactions is shown below.

[Formula 4]

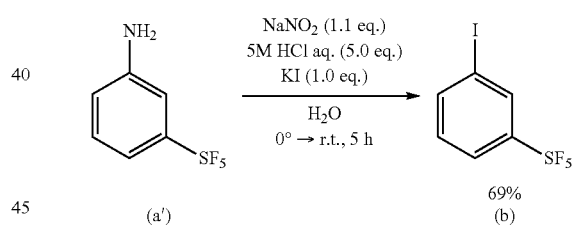

In this reaction, it is preferred that the amounts of $NaNO_2$, HCl and KI to be used be in the ranges of 1 to 1.5 equivalent, 2 to 8 equivalent, and 1 to 1.5 equivalent, respectively, relative to the compound (a'). The type of a solvent is not limited but water is preferred. The reaction temperature can be adjusted as appropriate but is preferably in the range of 0° C. to room temperature.

(2) Synthesis of a Diaryliodonium Salt (d)

The thus-prepared compound (b) is subjected to an oxidation reaction and a Friedel-Crafts reaction with a compound (c) at the same time. A preferred oxidant is a peroxide, with meta-chloroperbenzoic acid being particularly preferred. The amount of the oxidant to be used is preferably in the range of 1.0 to 1.5 equivalent relative to the compound (b).

The compound (c) is a benzene compound. In the compound (c), $R^2$ and n are as defined above. The amount of the compound (c) to be used is preferably in the range of 1.0 to 1.5 equivalent relative to the compound (b). The Friedel-Crafts reaction is performed in the presence of a Lewis acid, and from various viewpoints including reactivity and the solubility of a product in a solvent, it is preferred that the Lewis acid be trifluoromethanesulfonic acid. The amount of the Lewis acid to be used is preferably in the range of 1.0 to 2.5 equivalent relative to the compound (b).

The reaction temperature is not limited, and such reactions can be performed at a temperature of about 20 to 60° C., with room temperature being preferred. A preferred solvent is a halogenated hydrocarbon, with dichloromethane, etc. being more preferred. These reactions are described in *Chem. Commun.*, 2007, 2521, and *J. Am. Chem. Soc.*, 2011, 133, 13778. The compound of interest, diaryliodonium salt, can be purified by recrystallization with diethyl ether.

The diaryliodonium salt can also be synthesized via a Koser reagent (ArI(OH)OTs). The Koser reagent can be synthesized by preparing aryliodine(III) bis(trifluoroacetate) using Oxone® as an oxidant and treating it with p-toluenesulfonic acid (Viktor V. Zhdankin, et al., *J. Org. Chem.*, 2010, 75, 2119). The Koser reagent is generally solid and thus is very convenient to be stored as a synthetic intermediate. Then, the Koser reagent is subjected to a Friedel-Crafts reaction with the compound (c) in trifluoroethanol, whereby the diaryliodonium salt can be synthesized (Yasuyuki Kita, et al., *Chem. Commun.*, 2007, 4152).

The amount of the oxidant to be used in these reactions is in the range of 1.0 to 2.0 equivalent relative to the compound (b). The temperature of the oxidation reaction can be adjusted as appropriate but is preferably room temperature. Oxone® is an oxidant containing a potassium salt of persulfuric acid. The conditions, etc. for the Friedel-Crafts reaction are as described above. An example of these reactions is shown below.

[Formila 5]

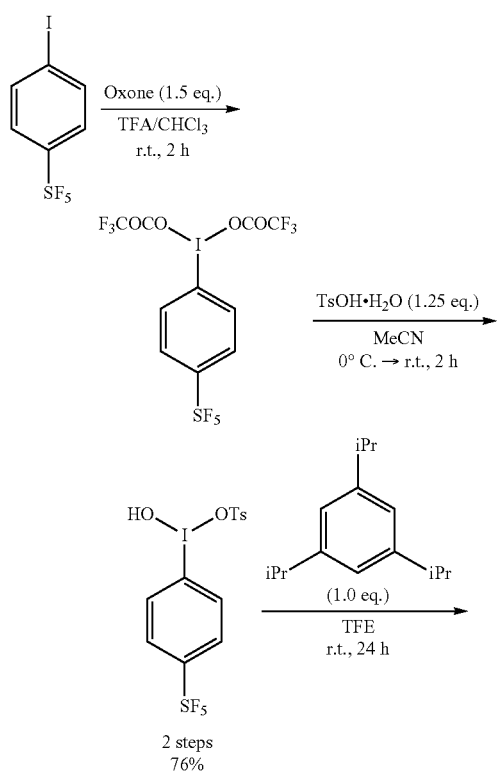

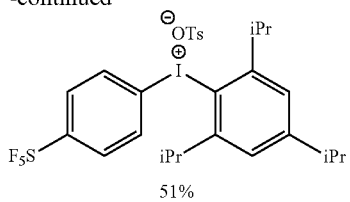

51%

3. Reaction Using the Diaryliodonium Salt

The diaryliodonium salt is reacted with a nucleophilic compound, whereby an ArSF$_5$ group can be introduced into the nucleophilic compound. This reaction can be represented by the following formula.

[Formula 6]

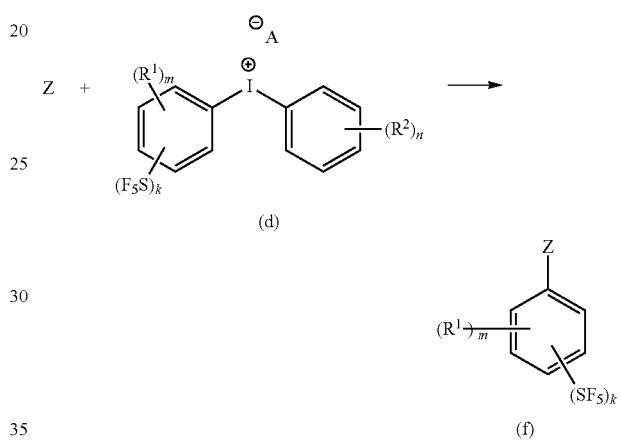

The nucleophilic compound is a compound having a nucleophilic moiety, and an ArSF$_5$ group can be introduced into the nucleophilic moiety by this reaction. Thus, in the present invention, the nucleophilic compound may also be called a "compound of interest". The reaction is preferably performed under such excessive conditions that the diaryliodonium salt is present in an amount of 1.1 to 2 equivalent relative to the nucleophilic compound Z. The reaction temperature can be adjusted as appropriate depending on the reactivity but is preferably in the range of about 20 to 160° C. The reaction solvent is also determined in consideration of reaction temperature and solubility, but a polar solvent such as water, an alcohol, NMP, DMF, or a halogenated hydrocarbon is preferred. A reaction promoter such as a base or metal can be used as appropriate depending on the nucleophilic compound.

Examples of the nucleophilic compound include a 1,3-dicarbonyl compound such as a β-keto ester or malonic acid, a phenol compound, an aniline compound, a heterocyclic compound, an alcohol compound, an oxyimide compound, an aromatic sulfur compound, and an aromatic cyanogen compound. Such compounds may also have a substituent. For example, the phenol compound can be exemplified by a phenol, an alkyl-substituted phenol, a halogenated phenol, or the like. The same holds true for other compounds. The reaction promoter used in the case of using a 1,3-dicarbonyl compound, a phenol compound, an alcohol compound, or an oxyimide compound is preferably a strong base such as sodium hydride, sodium hydroxide, or potassium tert-butoxide. The reaction promoter used in the case of using an aniline compound, a heterocyclic compound, an aromatic sulfur compound, or an aromatic cyanogen compound is preferably a metal such as palladium on carbon or copper trifluoromethanesulfonate.

As regards the reaction mechanism for this reaction, it is presumed that the reaction may proceed through a ligand coupling as shown below (Masahito Ochiai, et al., *ARKIVOC*, 2003, 43).

[Formula 7]

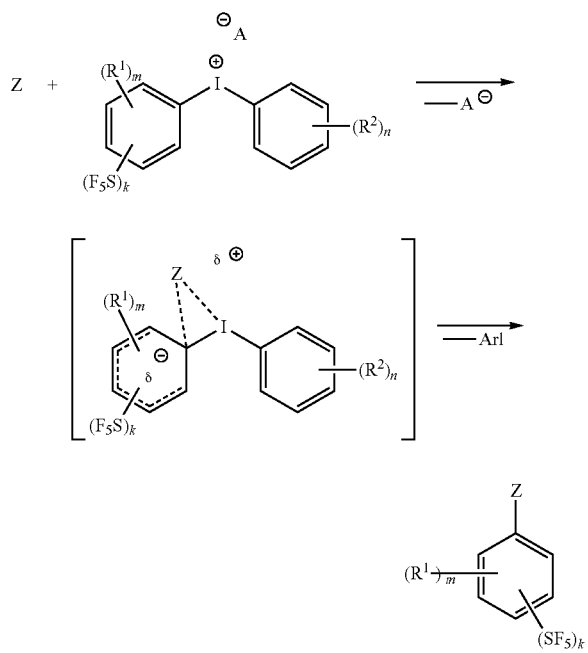

First, a nucleophilic compound Z may coordinate to the iodine atom I at the center due to detachment of a counter anion A. Then, through an intermediate like ipso-substitution, a ligand coupling may proceed in a selective manner for a more electron-deficient $SF_5$ aryl.

EXAMPLES

Example 1

The following reactions were performed to synthesize a diaryliodonium salt.

[Formula 8]

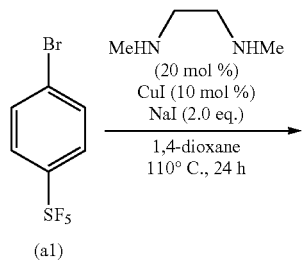

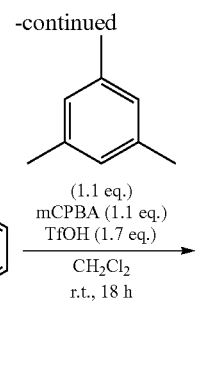

Copper(I) iodide (95.2 mg, 0.500 mmol, produced by Wako Pure Chemical Industries, Ltd.) and sodium iodide (1.5 g, 10.0 mmol, produced by Nacalai Tesque, Inc.) were charged into a Schlenk flask, and the flask was purged with argon. Then, aryl bromide (a1) (1.42 g, 5.00 mmol, produced by Ube Industries, Ltd.), N,N'-dimethylethylenediamine (108 μL, 1.00 mmol, produced by Sigma-Aldrich), and 1,4-dioxane (5.0 mL) were added, and the mixture was stirred at 110° C. for 24 hours. After completion of the reaction, the mixture was subjected to cooling to room temperature, followed by addition of an aqueous ammonia solution (28%) and water, and extraction with dichloromethane, and the organic phase was washed with a saturated sodium chloride solution and dried with sodium sulfate. Then, the residue after distilling off the solvent under reduced pressure was purified by silica gel column chromatography (hexane) to afford aryl iodide (b1) (1.48 g, 90%) as a white solid.

Meta-chloroperbenzoic acid (545 mg, 2.18 mmol, produced by Wako Pure Chemical Industries, Ltd.) was charged into an eggplant-shaped flask and dried under vacuum at room temperature for one hour, and then a dichloroethane solution (6.0 mL) of the aryl iodide (b1) (654 mg, 1.98 mmol) was added. Thereafter, the mixture was subjected to cooling to 0° C., followed by dropwise addition of trifluoromethanesulfonic acid (0.298 mL, 3.37 mmol, produced by Central Glass Co., Ltd.) and stifling at room temperature for 2 hours. Then, the mixture was subjected to cooling to 0° C., followed by dropwise addition of mesitylene (0.303 mL, 2.18 mmol, produced by Nacalai Tesque, Inc.) and stirring at room temperature for another 18 hours. After completion of the reaction, the solvent was distilled off under reduced pressure, diethyl ether was added to reprecipitate the product, and the solids were filtered off using a Kiriyama funnel and washed with diethyl ether. Finally, the solids were dried under vacuum to afford a diaryliodonium salt (d1) (1.0902 g, 92%) as a white solid.

Further, synthesis was carried out according to the same procedure using each of the following compounds as aryl iodide. The compounds are shown below together with their results for mass spectrometry and NMR analyses. In the present invention, mass spectrometry was performed using a DCMS-QP5050A spectrometer produced by Shimadzu Corporation, and $^1$H-NMR and $^{19}$F-NMR spectra were determined using a Mercury 300 spectrometer produced by Varian.

TABLE 1

Example 1

| Aryl iodide | Diaryliodonium salt |
|---|---|
|  a1 | 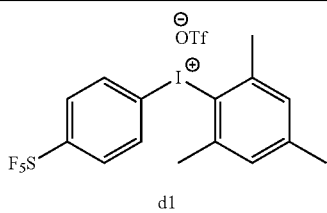 d1 Yield 83% |
| 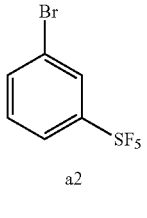 a2 | 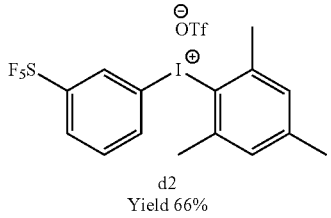 d2 Yield 66% |
| 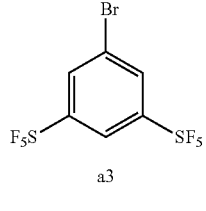 a3 | 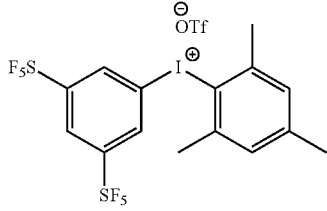 d3 Yield 43% |

[Formula 9]

Mesityl(4-(pentafluorosulfanyl)phenyl)iodonium trifluoromethanesulfonate (d1)

MS (ESI, m/z) 449 (M$^+$); $^1$H NMR (CDCl$_3$:DMSO-d$_6$=24:1, 300 MHz): δ=2.40 (s, 3H), 2.61 (s, 6H), 7.16 (s, 2H), 7.78 (m, 4H); $^{19}$F NMR (CDCl$_3$:DMSO-d$_6$=24:1, 282 MHz): δ=−167.7 (d, J=150.6 Hz, 4F), −148.8 (quintet, J=151.1 Hz, 1F), −78.7 (s, 3F); (2 steps) yield 83%

Mesityl(3-(pentafluorosulfanyl)phenyl)iodonium trifluoromethanesulfonate (d2)

MS (ESI, m/z) 449 (M$^+$); $^1$H NMR (CDCl$_3$, 300 MHz): δ=2.38 (s, 3H), 2.64 (s, 6H), 7.14 (s, 2H), 7.53 (t, J=8.0 Hz, 3H), 7.88-7.99 (m, 3H); $^{19}$F NMR (CDCl$_3$, 282 MHz): δ=−167.7 (d, J=150.3 Hz, 4F), −149.5 (quintet, J=149.9 Hz, 1F), −9.1 (s, 3F); (2 steps) yield 66%

Mesityl(3,5-bis(pentafluorosulfanyl)phenyl)iodonium trifluoromethanesulfonate (d3)

MS (ESI, m/z) 575 (M$^+$); $^1$H NMR (CDCl$_3$, 300 MHz): δ=2.40 (s, 3H), 2.65 (s, 6H), 7.18 (s, 2H), 8.20-8.21 (m, 3H); $^{19}$F NMR (CDCl$_3$, 282 MHz): δ=−166.8 (d, J=151.4 Hz, 4F), −151.1 (quintet, J=151.2 Hz, 1F), −78.8 (s, 3F); (2 steps) yield 43%

Example 2

The following reaction was performed to introduce an ArSF$_5$ group into a compound of interest.

[Formula 10]

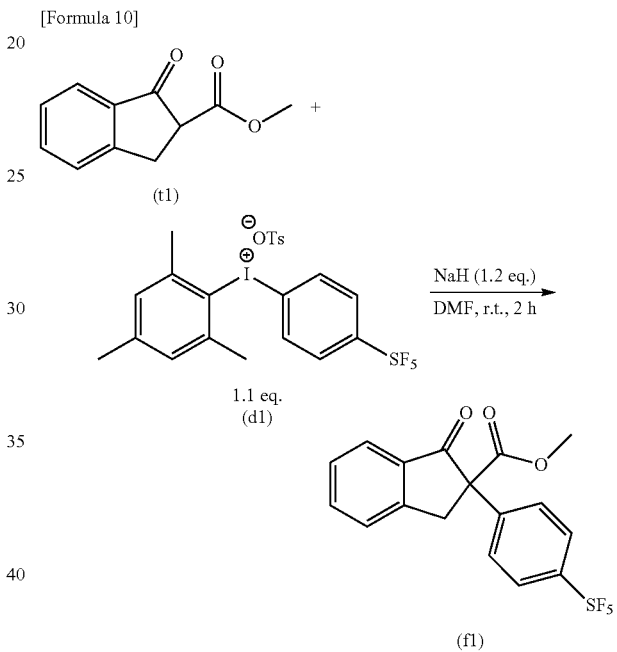

A β-keto ester (t1) (19.0 mg, 0.100 mmol) synthesized by the present inventors and sodium hydride (60%, 4.8 mg, 0.120 mmol, produced by Nacalai Tesque, Inc.) were stirred in N,N'-dimethylformamide (1.00 mL) for 10 minutes, and then the diaryliodonium salt (d1) (65.8 mg, 0.110 mmol) obtained in Example 1 was added and the mixture was stirred for another 2 hours. After completion of the reaction, water was added, the mixture was extracted with diethyl ether, and the organic phase was washed with an aqueous saturated sodium chloride solution and dried with sodium sulfate. Then, the residue after distilling off the solvent under reduced pressure was purified by silica gel column chromatography (hexane/ethyl acetate=9/1) to afford product (f1) (27.8 mg, 71%) as a white solid.

The same reaction was performed using each of the following source materials, whereby products (f2) to (f6) were prepared. The materials and products are shown below together with their analysis results.

[Table 2]
TABLE 2
| Example 2 | | |
|---|---|---|
| β-keto ester | Diaryliodonium salt | Product |
| 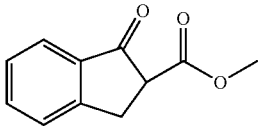 t1 | 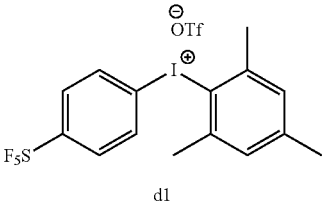 d1 | 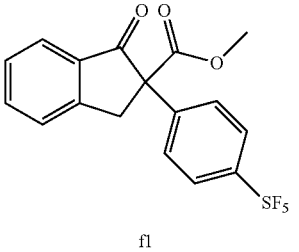 f1 |
| | 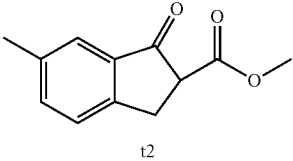 d2 | 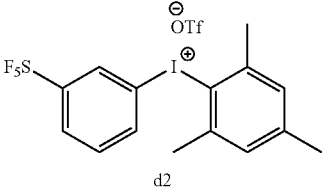 f2 |
| 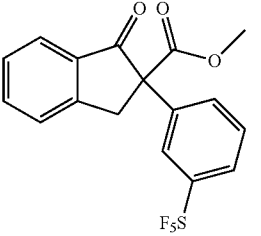 t2 | 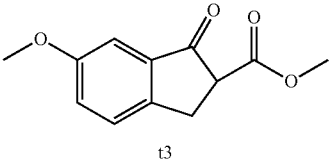 d1 | 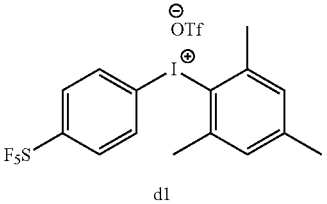 f3 |
| 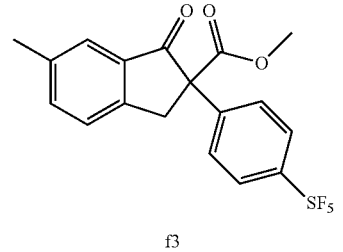 t3 | | 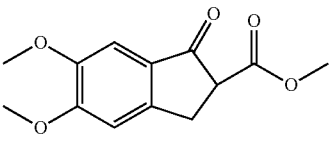 f4 |
| 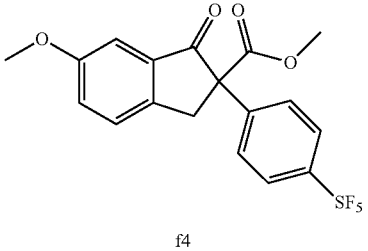 t4 | |  f5 |

TABLE 2-continued

Example 2

| β-keto ester | Diaryliodonium salt | Product |
|---|---|---|
| t5 (methyl 5-chloro-1-oxo-2,3-dihydro-1H-indene-2-carboxylate) | | f6 (methyl 5-chloro-2-(4-(pentafluorosulfanyl)phenyl)-1-oxo-2,3-dihydro-1H-indene-2-carboxylate) |

[Formula 11]

Methyl 2,3-dihydro-1-oxo-2-(4-(pentafluorosulfanyl)phenyl)-1H-indene-2-carboxylate (f1)

MS (EI, m/z) 392 (M⁺); $^1$H NMR (CDCl$_3$, 300 MHz): δ=3.56 (d, J=17.1 Hz, 1H), 3.76 (s 3H), 4.23 (d, J=17.4 Hz, 1H), 7.45 (t, J=7.4 Hz, 1H), 7.51-7.56 (m, 3H), 7.67 (d, J=7.4 Hz, 1H), 7.71-7.75 (m, 2H), 7.85 (d, J=8.1 Hz); $^{19}$F NMR (CDCl$_3$, 282 MHz): δ=−167.6 (d, J=150.3 Hz, 4F), −146.3 (quintet, J=150.4, 1F); yield 71%

Methyl 2,3-dihydro-1-oxo-2-(3-(pentafluorosulfanyl)phenyl)-1H-indene-2-carboxylate (f2)

MS (ESI, m/z) 415 [(M+Na)⁺]; $^1$H NMR (CDCl$_3$, 300 MHz): δ=3.57 (d, J=17.1 Hz, 1H), 3.74 (s, 3H), 4.24 (d, J=16.8 Hz, 1H), 7.45 (t, J=7.5 Hz, 2H), 7.53 (d, J=7.5 Hz, 1H), 7.62-7.71 (m, 3H), 7.84-7.87 (m, 2H); $^{19}$F NMR (CDCl$_3$, 282 MHz): δ=−167.7 (d, J=149.5 Hz, 4F), −146.3 (quintet, J=150.2, 1F); yield 89%

Methyl 6-methyl-2,3-dihydoro-1-oxo-2-(4-(pentafluorosulfanyl)phenyl)-1H-indene-2-carboxylate (f3)

MS (ESI, m/z) 429 [(M+Na)⁺]; $^1$H NMR (CDCl$_3$, 300 MHz): δ=2.43 (s, 3H), 3.51 (d, J=17.4 Hz, 1H), 3.75 (s, 3H), 4.17 (d, J=17.4 Hz, 1H), 7.40 (d, J=6.8 Hz, 1H), 7.49-7.54 (m, 3H), 7.65 (s, 1H), 7.72 (d, J=8.4 Hz, 2H); $^{19}$F NMR (CDCl$_3$, 282 MHz): δ=−167.2 (d, J=150.3 Hz, 4F), −146.3 (quintet, J=150.4, 1F); yield 49%

[Formula 12]

Methyl 6-methoxy-2,3-dihydro-1-oxo-2-(4-(pentafluorosulfanyl)phenyl)-1H-indene-2-carboxylate (f4)

MS (ESI, m/z) 445 [(M+Na)⁺]; $^1$H NMR (CDCl$_3$, 300 MHz): δ=3.48 (d, J=16.8 Hz, 1H), 3.75 (s, 3H), 3.85 (s, 3H), 4.13 (d, J=17.1 Hz, 1H), 7.26-7.29 (m, 2H), 7.40 (d, J=8.4 Hz 1H), 7.52 (d, J=8.7 Hz, 2H), 7.72 (d, J=8.7 Hz, 2H); $^{19}$F NMR (CDCl$_3$, 282 MHz): δ=−167.7 (d, J=150.3 Hz, 4F), −146.4 (quintet, J=150.2, 1F); yield 65%

Methyl 5,6-dimethoxy-2,3-dihydro-1-oxo-2-(3-(pentafluorosulfanyl)phenyl)-1H-indene-2-carboxylate (f5)

MS (ESI, m/z) 475 [(M+Na)⁺]; $^1$H NMR (CDCl$_3$, 300 MHz): δ=3.41 (d, J=17.1 Hz, 1H), 3.76 (s, 3H), 3.93 (s, 3H), 4.00 (s, 3H), 4.15 (d, J=17.1 Hz, 1H), 6.91 (s, 1H), 7.24 (s, 1H) 7.51 (d, J=8.1 Hz, 2H), 7.72 (d, J=9.0 Hz, 2H); $^{19}$F NMR (CDCl$_3$, 282 MHz): δ=−167.6 (d, J=149.5 Hz, 4F), −146.4 (quintet, J=150.2, 1F); yield 65%

Methyl 5-chloro-2,3-dihydro-1-oxo-2-(4-(pentafluorosulfanyl)phenyl)-1H-indene-2-carboxylate (f6)

MS (ESI, m/z) 449 [(M+Na)⁺]; $^1$H NMR (CDCl$_3$, 300 MHz): δ=3.52 (d, J=17.4 Hz, 1H), 3.75 (s, 3H), 4.22 (d, J=17.4 Hz, 1H), 7.44 (d, J=8.1 Hz, 1H), 7.52-7.54 (m, 3H), 7.72-7.80 (m, 3H); $^{19}$F NMR (CDCl$_3$, 282 MHz): δ=−167.7 (d, J=150.6 Hz, 4F), −146.6 (quintet, J=150.2, 1F); yield 66%

Example 3

The following reaction was performed to introduce an ArSF$_5$ group into a compound of interest.

[Formula 13]

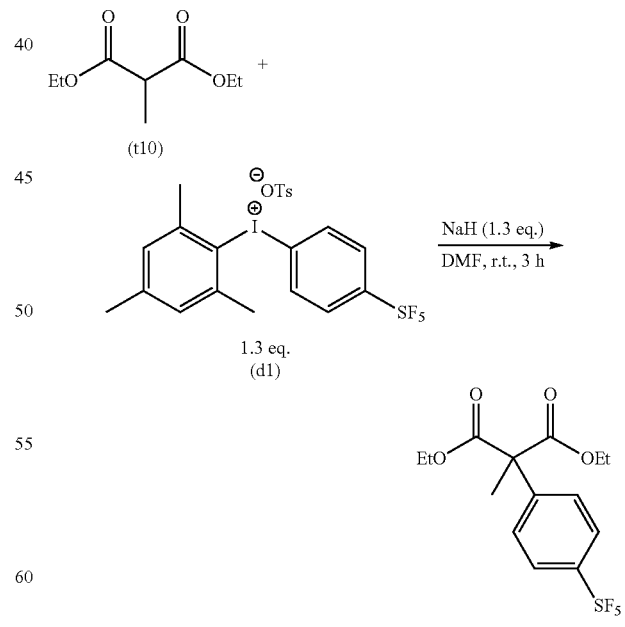

Malonic ester (t10) (51.3 μL, 0.300 mmol, produced by Tokyo Chemical Industry Co., Ltd.) was dissolved in N,N'-dimethylformamide (0.39 mL). A mixture of sodium hydride (60%, 15.6 mg, 0.390 mmol, produced by Nacalai Tesque, Inc.) and N,N'-dimethylformamide (0.39 mL) was provided, and the malonic ester solution prepared earlier was added at 0° C. to the mixture. Then, after the mixture was stirred at 0° C. for 10 minutes, a mixture of the diaryliodonium salt (d1) (233 mg, 0.390 mmol) obtained in Example 1 and N,N'-dimethylformamide (0.39 mL) was added, and the resultant mixture was stirred at room temperature for another 3 hours. After completion of the reaction, water was added, the mixture was extracted with diethyl ether, and the organic phase was washed with an aqueous saturated sodium chloride solution and dried with sodium sulfate. Then, the residue after distilling off the solvent under reduced pressure was purified by silica gel column chromatography (hexane/ethyl acetate=9/1) to afford product (f10) (95.2 mg, 84%) as a colorless oily product.

The same reaction was performed using (d2) as a diaryliodonium salt, whereby product (f11) was obtained. The materials and products are shown below together with their analysis results.

[Table 3]

TABLE 3

Example 3

| Malonic ester | Diaryliodonium salt | Product |
|---|---|---|
| t10 | d1 | f10 |
| | d2 | f11 |

[Formula 14]

Diethyl 2-methyl-2-(3-(pentafluorosulfanyl)phenyl)malonate (f10)

MS (ESI, m/z) 399 [(M+Na)$^+$]; $^1$H NMR (CDCl$_3$, 300 MHz): δ=1.27 (t, J=6.9 Hz, 6H), 1.88 (s, 3H), 4.25 (q, J=6.6 Hz, 4H), 7.49 (d, J=7.8 Hz, 2H), 7.73 (d, J=8.7 Hz, 2H); $^{19}$F NMR (CDCl$_3$, 282 MHz): δ=−167.6 (d, J=149.5 Hz, 4F), −146.2 (quintet, J=150.4, 1F); yield 84%

Diethyl 2-methyl-2-(3-(pentafluorosulfanyl)phenyl)malonate (f11)

MS (ESI, m/z) 399 [(M+Na)$^+$]; $^1$H NMR (CDCl$_3$, 300 MHz): δ=1.24-1.34 (m, 6H), 1.89 (s 3H), 4.21-4.31 (m, 4H), 7.45 (t, J=7.5 Hz, 1H), 7.56 (d, J=7.8 Hz, 1H), 7.71 (d, J=7.8 Hz, 1H), 7.82 (s, 1H); $^{19}$F NMR (CDCl$_3$, 282 MHz): δ=−167.6 (d, J=150.3 Hz, 4F), −146.1 (quintet, J=150.4, 1F); yield 52%

Example 4

The following reaction was performed to introduce an ArSF$_5$ group into a compound of interest.

[Formula 15]

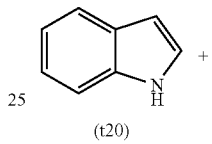

(t20)

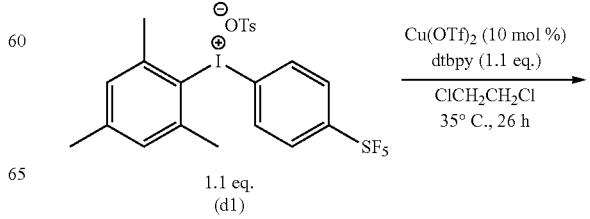

17
-continued

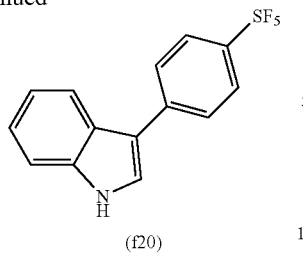

(f20)

There was provided a 1,2-dichloroethane (0.5 mL) solution of indole (t20) (11.7 mg, 0.100 mmol, produced by Nacalai Tesque, Inc.), copper(II) trifluoromethanesulfonate (3.6 mg, 0.010 mmol, produced by Tokyo Chemical Industry Co., Ltd.), and the diaryliodonium salt (d1) (65.8 mg, 0.110 mmol) obtained in Example 1. To the solution was added 2,6-di-tert-butylpyridine (24.7 μL, 0.110 mmol, produced by Sigma-Aldrich), and the mixture was stirred at 35° C. for 26 hours. After completion of the reaction, a saturated ammonium chloride solution was added, the mixture was extracted with dichloromethane, and the organic phase was washed with an aqueous saturated sodium chloride solution and dried with sodium sulfate. Then, the residue after distilling off the solvent under reduced pressure was purified by silica gel column chromatography (hexane/ethyl acetate=8/2) to afford product (f20) (13.7 mg, 43%) as a yellow solid.

Example 5

The following reaction was performed to introduce an ArSF$_5$ group into a compound of interest.

[Chem. 16]

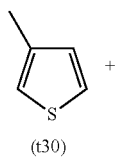

(t30)

18
-continued

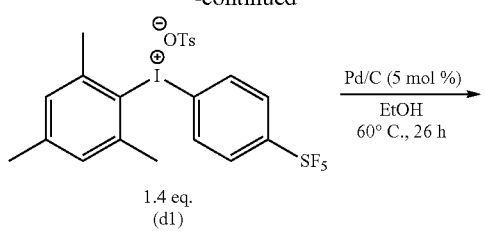

1.4 eq.
(d1)

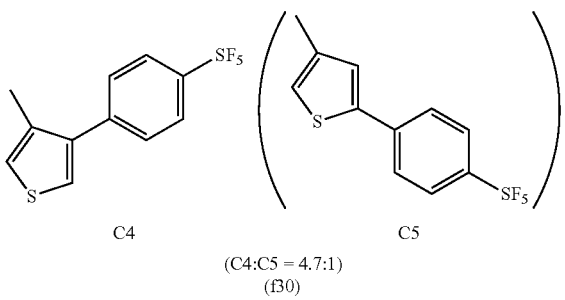

C4        C5

(C4:C5 = 4.7:1)
(f30)

There was provided a mixture of palladium on carbon (5 wt %, 10.6 mg, 0.005 mmol, produced by Sigma-Aldrich), the diaryliodonium salt (d1) (83.8 mg, 0.140 mmol), and ethanol (0.5 mL). And 3-methylthiophene (t30) (9.7 μL, 0.100 mmol, produced by Sigma-Aldrich) was added to the mixture, which was then stirred under argon atmosphere at 60° C. for 26 hours. After completion of the reaction, insoluble matters were removed by filtration on silica gel, and the dissolved matter was washed with ethyl acetate. In this reaction, adducts to the carbon atoms at the 4th and 5th positions of methylthiophene were generated at a (molar) ratio of 4.7:1. The reaction mixture containing these adducts was then subjected to distillation off of the solvent under reduced pressure and purification by silica gel column chromatography (hexane/ethyl acetate=98/2) to afford the adduct to the 4th position (product (f30)) (8.3 mg, 28%) as a colorless oily product. The materials, products, and their analysis results in this example are shown below together with those in Example 4.

[Table 4]

TABLE 4

| Examples 4 and 5 | | |
|---|---|---|
| Compound of interest | Diaryliodonium salt | Product |
| t20 | d1 | f20 |

TABLE 4-continued

Examples 4 and 5

| Compound of interest | Diaryliodonium salt | Product |
|---|---|---|
|  t30 | | 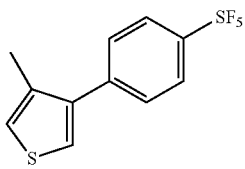 f30 |

[Formula 17]

3-(4-(Pentafluorosulfanyl)phenyl)-1H-indole (f20)

MS (EI, m/z) 319 (M$^+$); $^1$H NMR (CDCl$_3$, 300 MHz): δ=7.21-7.32 (m, 2H), 7.46-7.48 (m, 2H), 7.74 (d, J=8.7 Hz, 2H), 7.82 (d, J=8.7 Hz, 2H), 7.92 (d, J=7.8 Hz, 2H), 8.37 (brs, 1H); $^{19}$F NMR (CDCl$_3$, 282 MHz) δ=−167.2 (d, J=150.6 Hz, 4F), −145.0 (quintet, J=150.0 Hz, 1F); yield 43%

3-Methyl-4-(4-(pentafluorosulfanyl)phenyl)thiophene (f30)

MS (EI, m/z) 300 (M$^+$); $^1$H NMR (CDCl$_3$, 300 MHz): δ=2.28 (s, 3H), 7.07 (s, 1H), 7.26 (s, 1H), 7.48 (d, J=7.8 Hz, 2H), 7.79 (d, J=8.4 Hz, 2H); $^{19}$F NMR (CDCl$_3$, 282 MHz) δ=−167.4 (d, J=150.3 Hz, 4F) −145.7 (quintet, J=150.4 Hz, 1F); yield 28%

Example 6

The following reaction was performed to introduce an ArSF$_5$ group into a compound of interest.

[Formula 18]

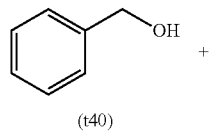

(t40)

+

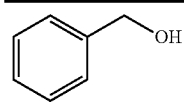

1.1 eq.
(d1)

NaOH (2.0 eq.)
H$_2$O, 50° C., 3 h

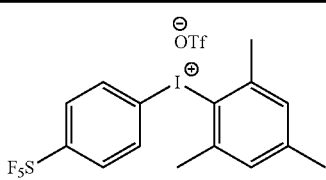

(f40)

To a solution of sodium hydroxide (16.0 mg, 0.400 mmol) in water (1.0 mL), benzyl alcohol (t40) (20.6 μL, 0.200 mmol, produced by Nacalai Tesque, Inc.) was added, and the mixture was stirred at room temperature for 5 minutes. Thereafter, the diaryliodonium salt (d1) (144 mg, 0.390 mmol) was added to the mixture, which was then stirred at 50° C. for another 3 hours. After completion of the reaction, water was added, the mixture was extracted with ethyl acetate, and the organic phase was washed with an aqueous saturated sodium chloride solution and dried with sodium sulfate. Then, the residue after distilling off the solvent under reduced pressure was purified by silica gel column chromatography (hexane/ethyl acetate=95/5) to afford product (f40) (43.6 mg, 70%) as a white solid.

The same reaction was performed using the following compound, whereby a product was prepared. The compounds and products are shown below together with their analysis results.

[Table 5]

TABLE 5

Example 6

| Compound of interest | Diaryliodonium salt | Product |
|---|---|---|
| 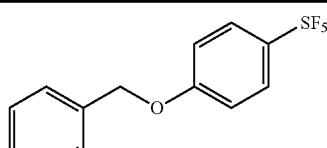 t40 | d1 | f40 |

TABLE 5-continued

Example 6

| Compound of interest | Diaryliodonium salt | Product |
| --- | --- | --- |
| | d2 | f41 |

[Formula 19]

1-(Benzyloxy)-4-(pentafluorosulfanyl)benzene (f40)

MS (EI, m/z) 310 (M$^+$); $^1$H NMR (CDCl$_3$, 300 MHz): δ=5.11 (s, 2H), 6.98 (d, J=8.4 Hz, 1H), 7.41 (m, 5H), 7.68 (d, J=7.8 Hz, 2H); $^{19}$F NMR (CDCl$_3$, 282 MHz): δ=−166.2 (d, J=150.3 Hz, 4F), −144.4 (quintet, J=150.4 Hz, 1F); yield 70%

1-(Benzyloxy)-3-(pentafluorosulfanyl)benzene (f41)

MS (EI, m/z) 310 (M$^+$); $^1$H NMR (CDCl$_3$, 300 MHz): δ=5.09 (s, 2H), 7.10 (s, 1H), 7.35-7.42 (m, 8H); $^{19}$F NMR (CDCl$_3$, 282 MHz): δ=−167.8 (d, J=149.5 Hz, 4F), −146.0 (quintet, J=150.1 Hz, 1F); yield 72%

Example 7

The same reaction as in Example 6 was performed except that phenol (t50) (produced by Tokyo Chemical Industry Co., Ltd.) was used instead of benzyl alcohol. The results are summarized below.

[Table 6]

TABLE 6

Example 7

| Compound of interest | Diaryliodonium salt | Product |
| --- | --- | --- |
| t50 | d1 | f50 |
| | d2 | f51 |

[Formula 20]

1-(Pentafluorosulfanyl)-4-phenoxybenzene (f50)

MS (EI, m/z) 296 (M$^+$); $^1$H NMR (CDCl$_3$, 300 MHz): δ=6.99 (d, J=8.7 Hz, 2H), 7.05-7.08 (m, 2H), 7.19-7.26 (m, 1H), 7.38-7.44 (m, 2H), 7.70 (dd, J=9.0 Hz, 1.8 Hz, 2H); $^{19}$F NMR (CDCl$_3$, 282 MHz): δ=−166.0 (d, J=150.3 Hz, 4F), −144.6 (quintet, J=150.40 Hz, 1F); yield 77%

1-(Pentafluorosulfanyl)-3-phenoxybenzene (f51)

MS (EI, m/z) 296 (M$^+$); $^1$H NMR (CDCl$_3$, 300 MHz): δ=7.02-7.05 (m, 2H), 7.10-7.13 (m, 1H), 7.16-7.26 (m, 1H), 7.36-7.49 (m, 5H); $^{19}$F NMR (CDCl$_3$, 282 MHz): δ=−167.8 (d, J=149.5 Hz, 4F), −146.6 (quintet, J=150.2, 1F); yield 24%

Example 8

The following reaction was performed to introduce an ArSF$_5$ group into a compound of interest.

[Formula 21]

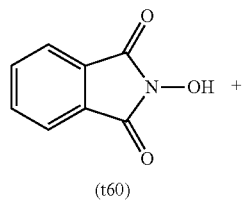

(t60)

mixture was extracted with ethyl acetate, and the organic phase was washed with an aqueous saturated sodium chloride solution and dried with sodium sulfate. Then, the residue after distilling off the solvent under reduced pressure was purified by silica gel column chromatography (hexane/ethyl acetate=8/2) to afford product (f60) (48.5 mg, 66%) as a pale yellow solid.

The same reaction was performed using (d2) as a diaryliodonium salt. The materials and products are shown below together with their analysis results.

[Table 7]

TABLE 7

Example 8

| Compound of interest | Diaryliodonium salt | Product |
| --- | --- | --- |
| t60 | d1 | f60 |
| | d2 | f61 |

An N,N-dimethylformamide (0.8 mL) solution of N-hydroxyphthalimide (t60) (32.6 mg, 0.200 mmol, produced by Nacalai Tesque, Inc.) and tert-butoxypotassium (24.7 mg, 0.220 mmol, produced by Tokyo Chemical Industry Co., Ltd.) was stirred at room temperature for 10 minutes. Then, the diaryliodonium salt (d1) (132 mg, 0.220 mmol) was added to the solution, which was then stirred at 60° C. for another 2 hours. After completion of the reaction, water was added, the

[Formula 22]

2-(4-(Pentafluorosulfanyl)phenoxy)isoindoline-1,3-dione (f61)

MS (EI, m/z) 365 (M$^+$); $^1$H NMR (CDCl$_3$, 300 MHz): δ=7.21 (d, J=9.0 Hz, 2H), 7.76 (d, J=9.3 Hz, 2H), 7.84-7.87 (m, 2H), 7.94-7.97 (m, 2H); $^{19}$F NMR (CDCl$_3$, 282 MHz): δ=−166.6 (d, J=150.3 Hz, 4F), −146.1 (quintet, J=−150.7, 1F); yield 66%

2-(3-(Pentafluorosulfanyl)phenoxy)isoindoline-1,3-dione (f61)

MS (EI, m/z) 365 [M$^+$]; $^1$H NMR (CDCl$_3$, 300 MHz): δ=7.33 (d, J=8.4 Hz, 1H), 7.46 (t, J=8.1 Hz, 1H), 7.55-7.61 (m, 2H), 7.83-7.86 (m, 2H), 7.93-7.95 (m, 2H); $^{19}$F NMR (CDCl$_3$, 282 MHz): δ=−167.6 (d, J=150.6 Hz, 4F), −147.3 (quintet, J=−150.7, 1F); yield 88%

Example 9

The following reaction was performed to introduce an ArSF$_5$ group into a compound of interest.

[Formula 23]

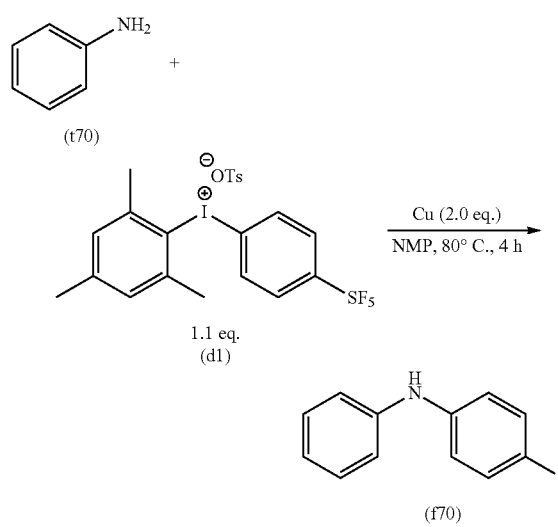

A suspension of aniline (t70) (18.3 μL, 0.200 mmol, produced by Kishida Chemical Co., Ltd.) and copper powder (25.4 mg, 0.400 mmol, produced by Hayashi Pure Chemical Ind., Ltd.) in N-methyl-2-pyrrolidone (0.4 mL) was stirred at room temperature for 15 minutes. Then, the diaryliodonium salt (d1) (132 mg, 0.220 mmol) was added to the suspension, which was then stirred at 80° C. for another 4 hours. After completion of the reaction, insoluble matters were removed by filtration on silica gel, and the dissolved matter was washed with diethyl ether. Then, the residue after distilling off the solvent under reduced pressure was purified by silica gel column chromatography (hexane/ethyl acetate=9/1) to afford product (f70) (32.3 mg, 55%) as a yellow solid.

The same reaction was performed using (d2) as a diaryliodonium salt. The materials and products are shown below together with their analysis results.

[Table 8]

[Formula 24]

4-(Pentafluorosulfanyl)phenyl-N-phenylaniline (f70)

MS (ESI, m/z) 330 [(M−Cl)$^-$]; $^1$H NMR (CDCl$_3$, 300 MHz): δ=5.95 (brs, 1H), 6.96 (d, J=8.7 Hz, 2H), 7.09 (t, J=7.4 Hz, 1H), 7.15 (d, J=8.1 Hz, 2H), 7.34 (t, J=7.5 Hz, 2H), 7.59 (d, J=9.3 Hz, 2H); $^{19}$F NMR (CDCl$_3$, 282 MHz): δ=−166.2 (d, J=150.5 Hz, 4F), −143.4 (quintet, J=−150.4, 1F); yield 55%

3-(Pentafluorosulfanyl)phenyl-N-phenylaniline (f71)

MS (ESI, m/z) 317 [(M+Na)$^+$]; $^1$H NMR (CDCl$_3$, 300 MHz): δ=5.84 (brs, 1H), 7.03-7.16 (m, 5H), 7.26-7.32 (m, 3H), 7.40 (s, 1H); $^{19}$F NMR (CDCl$_3$, 282 MHz): δ=−168.1 (d, J=149.5 Hz, 4F), −145.6 (quintet, J=−149.9, 1F); yield 69%

Example 10

The following reaction was performed to introduce an ArSF$_5$ group into a compound of interest.

[Formula 25]

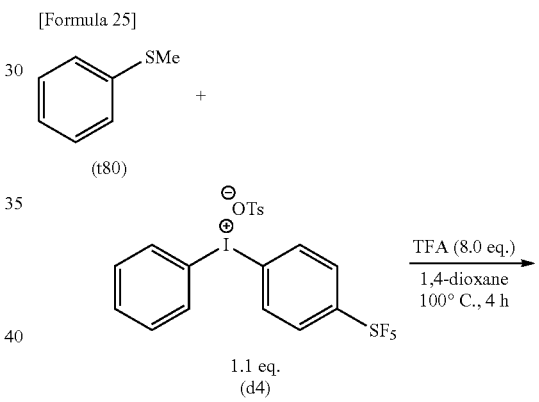

TABLE 8

| Example 9 |
|---|
| Compound of interest | Diaryliodonium salt | Product |
| t70 (aniline with NH$_2$) | d1 | f70 |
| t70 (aniline with NH$_2$) | d2 | f71 |

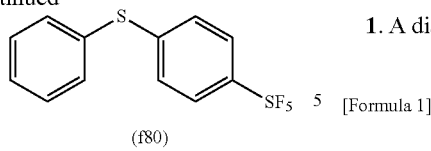

(f80)

There was first provided a diaryliodonium salt (d4). This compound was synthesized by performing the same reaction as in Example 1 except that benzene was used instead of mesitylene and that the reaction temperature was changed from room temperature to 80° C. Thereafter, there was provided a mixture of thioanisole (t80) (11.7 μL, 0.100 mmol, produced by Tokyo Chemical Industry Co., Ltd.) with the diaryliodonium salt (d4) (55.6 mg, 0.100 mmol) and 1,4-dioxane (0.32 mL). And trifluoroacetic acid (61.2 μL, 0.800 mmol) was added to the mixture, which was then stirred at 110° C. for 60 hours. After completion of the reaction, water was added, the mixture was extracted with diethyl ether, and the organic phase was washed with an aqueous saturated sodium chloride solution and dried with sodium sulfate. Then, the residue after distilling off the solvent under reduced pressure was purified by silica gel column chromatography (hexane) to afford product (f80) (5.7 mg, 18%) as a colorless oily product. The results are summarized below.

[Table 9]

TABLE 9

Example 10

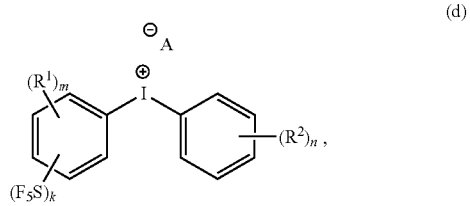

[Formula 26]

(4-(Pentafluorosulfanyl)phenyl) (phenyl)sulfane (f80)

MS (EI, m/z) 312 (M$^+$); $^1$H NMR (CDCl$_3$, 300 MHz): δ=7.19 (d, J=7.8 Hz, 2H), 7.40-7.42 (m, 3H), 7.48-7.52 (m, 2H), 7.58-7.62 (m, 2H); $^{19}$F NMR (CDCl$_3$, 282 MHz): δ=−167.3 (d, J=150.3 Hz, 4F), −145.7 (quintet, J=−150.2, 1F); yield 18%

It is demonstrated that the present invention allows the introduction of a pentafluorosulfanylphenyl group into different compounds of interest. This invention, which enables a pentafluorosulfanylphenyl group to be introduced into an sp$^3$ carbon in a compound of interest, is useful for physiological substances including such combined pharmaceuticals. This invention also allows the introduction of a pentafluorosulfanylphenyl group into an oxygen or nitrogen atom in a compound of interest.

What is claimed is:

1. A diaryliodonium salt of the general formula (d):

[Formula 1]

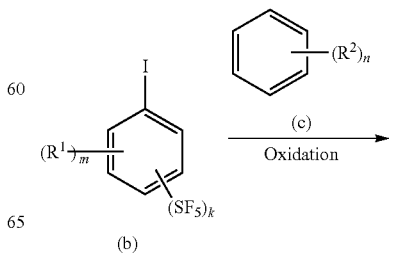

wherein k is 1 or 2, R$^1$ is an alkyl group having 1 or 2 carbon atoms, m is an integer of 0 to 4, R$^2$ is a straight or branched alkyl group having 1 to 4 carbon atoms, n is an integer of 0 to 5, and A$^-$ is a counter anion.

2. The diaryliodonium salt according to claim 1, wherein m is 0, and n is 3.

3. The diaryliodonium salt according to claim 2, wherein R$^2$ is a methyl group, an ethyl group, a n-propyl group, or an i-propyl group.

4. The diaryliodonium salt according to claim 1, wherein m is 0, and n is 0.

5. A process for preparing the diaryliodonium salt according to any one of claims 1 to 4, the process comprising:

providing a compound of the general formula (b); and subjecting said compound to an oxidation reaction and a Friedel-Crafts reaction with a compound of the general formula (c) at the same time to produce the diaryliodonium salt of the general formula (d):

[Formula 2]

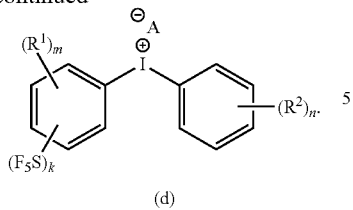

(d)

6. A process for preparing a compound of the general formula (f), the process comprising reacting a compound of the general formula (d) with a nucleophilic compound Z to introduce an aryl group containing a pentafluorosulfanyl group into the nucleophilic compound:

[Formula 3]

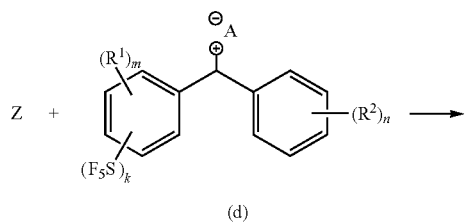

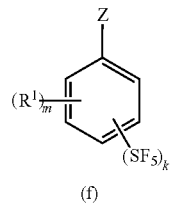

(f)

wherein $R^2$, n, $A^-$, $R^1$, m, and k are as defined in claim 1.

7. The process according to claim 6, wherein the nucleophilic compound Z is selected from the group consisting of a 1,3-dicarbonyl compound, a phenol compound, an aniline compound, a heterocyclic compound, an alcohol compound, an oxyimide compound, an aromatic sulfur compound, and an aromatic cyanogen compound.

\* \* \* \* \*